United States Patent
Haws et al.

(10) Patent No.: US 10,108,775 B2
(45) Date of Patent: *Oct. 23, 2018

(54) FEATURE SELECTION FOR EFFICIENT EPISTASIS MODELING FOR PHENOTYPE PREDICTION

(71) Applicant: International Business Machines Corporation, Armonk, NY (US)

(72) Inventors: David Haws, New York, NY (US); Dan He, Ossining, NY (US); Laxmi P. Parida, Mohegan Lake, NY (US)

(73) Assignee: International Business Machines Corporation, Armonk, NY (US)

( * ) Notice: Subject to any disclaimer, the term of this patent is extended or adjusted under 35 U.S.C. 154(b) by 1088 days.

This patent is subject to a terminal disclaimer.

(21) Appl. No.: 14/030,743

(22) Filed: Sep. 18, 2013

(65) Prior Publication Data

US 2014/0207436 A1    Jul. 24, 2014

Related U.S. Application Data

(63) Continuation of application No. 13/745,914, filed on Jan. 21, 2013.

(51) Int. Cl.
*G06F 19/00* (2018.01)
*G06F 19/12* (2011.01)
(Continued)

(52) U.S. Cl.
CPC .............. *G06F 19/12* (2013.01); *G06F 19/18* (2013.01); *G06F 19/24* (2013.01)

(58) Field of Classification Search
CPC .......... G06F 19/00; G06F 19/18; G06F 19/24; G06F 19/12; G06F 19/28; G06F 7/08;
(Continued)

(56) References Cited

U.S. PATENT DOCUMENTS 7,421,417 B2   9/2008   Mangasarian et al.
7,500,216 B1   3/2009   Blunno et al.
(Continued)

FOREIGN PATENT DOCUMENTS

JP   2006503346   1/2006
JP   2006048429   2/2006
(Continued)

OTHER PUBLICATIONS

Zhisong H., et al., "Prediciting Drug-Target Interaction Networks Based on Functional Groups and Biological Features," PLos One, Mar. 2010, pp. 1-8, vol. 5 Issue 3.
(Continued)

*Primary Examiner* — Mary K Zeman
(74) *Attorney, Agent, or Firm* — Fleit Gibbons Gutman Bongini Bianco PL; Thomas S. Grzesik

(57) ABSTRACT

Various embodiments select markers for modeling epistasis effects. In one embodiment, a processor receives a set of genetic markers and a phenotype. A relevance score is determined with respect to the phenotype for each of the set of genetic markers. A threshold is set based on the relevance score of a genetic marker with a highest relevancy score. A relevance score is determined for at least one genetic marker in the set of genetic markers for at least one interaction between the at least one genetic marker and at least one other genetic marker in the set of genetic markers. The at least one interaction is added to a top-k feature set based on the relevance score of the at least one interaction satisfying the threshold.

11 Claims, 2 Drawing Sheets

(51) Int. Cl.
*G06F 19/18* (2011.01)
*G06F 19/24* (2011.01)

(58) Field of Classification Search
CPC ...... G06F 17/3053; G06F 19/22; G06F 19/26; G06F 19/30; G06F 19/345; G06N 3/126; G06N 7/005
See application file for complete search history.

(56) References Cited

U.S. PATENT DOCUMENTS

| | | | |
|---|---|---|---|
| 7,624,074 | B2 | 11/2009 | Weston et al. |
| 2006/0088208 | A1 | 4/2006 | Nako et al. |
| 2006/0253427 | A1 | 11/2006 | Wu et al. |
| 2007/0122001 | A1 | 5/2007 | Wang et al. |
| 2007/0168306 | A1 | 7/2007 | Li et al. |
| 2007/0216675 | A1 | 9/2007 | Sun et al. |
| 2010/0082513 | A1 | 4/2010 | Liu |
| 2010/0287093 | A1 | 11/2010 | He et al. |
| 2010/0332430 | A1 | 12/2010 | Caraviello et al. |
| 2011/0038515 | A1 | 2/2011 | Jacquin et al. |
| 2011/0072130 | A1 | 3/2011 | Jiang et al. |
| 2011/0246409 | A1 | 10/2011 | Mitra |
| 2011/0307437 | A1 | 12/2011 | Aliferis et al. |
| 2012/0088981 | A1 | 4/2012 | Liu et al. |
| 2012/0177280 | A1 | 7/2012 | Zhukov et al. |
| 2012/0290607 | A1 | 11/2012 | Bhargava et al. |
| 2012/0310863 | A1 | 12/2012 | Crockett et al. |
| 2013/0109995 | A1 | 5/2013 | Rothman et al. |
| 2013/0150257 | A1 | 6/2013 | Abdueva et al. |
| 2013/0184603 | A1 | 7/2013 | Rothman |
| 2013/0231258 | A1 | 9/2013 | Wilde et al. |
| 2014/0064581 | A1 | 3/2014 | Madabhushi et al. |
| 2014/0278981 | A1 | 9/2014 | Mersov et al. |

FOREIGN PATENT DOCUMENTS

| | | |
|---|---|---|
| JP | 2008503589 | 2/2008 |
| JP | 2009523285 | 6/2009 |
| JP | 2010224815 | 10/2010 |
| JP | 2011180120 | 9/2011 |
| JP | 2012502398 | 1/2012 |
| WO | WO2012097152 | 7/2012 |

OTHER PUBLICATIONS

Kachel, A., et al., "Infosel++: Information Based Feature Selection C++ Library," 10th International Conference: Artificial Intelligence and Soft Computing, Jun. 2010, pp. 1-9.
Liu, H., "Evolving Feature Selection," Trends and Controversies, Nov. and Dec. 2005, pp. 1-13.
Zhisong, H., et al., "Computational Analysis of Protein Tyrosine Nitration," The Fourth International Conference on Computational Systems Biology, Sep. 9-11, 2010, pp. 1-8.
Premebida, C., et al., "Exploiting LIDAR-based features on Pedestrian Detection in Urban Scenarios," Proceedings of the 12th International IEEE Conference on Intelligent Transportation Systems, Oct. 3-7, 2009, pp. 1-6.
Mundra, P., et al., "SVM-RFE With MRMR Filter for Gene Selection," IEEE Transactions on Nanobioscience, Mar. 2010, pp. 1-7. vol. 7, Issue 1.
Liu, H., et al., "Feature Selection with dynamic mutual information," Pattern Recognition, Oct. 2008, pp. 1-10, vol. 42.
Estevez, P., et al., "Normalized Mutual Information Feature Selection," IEEE Transactions on Neural Networks, Feb. 2009, pp. 1-13. vol. 20, Issue 02.
Zhang, Z. et al, "MRMR Optimized Classification for Automatic Glaucoma Diagnosis", 33rd Annual Conference of the IEEE, EMBS, Aug. 30-Sep. 3, 2011, pp. 6228-6231.
Yang, Y., et al., "Recursive Feature Selection Based on Minimum Redundancy Maximum Relevancy", PAAP, Dec. 18-10, 2010, pp. 281-285.
Yang, X., et al., "Feature Selection for Computer-Aided Polyp Detection using MRMR," SPIE 7624, Medical Imaging, Feb. 13, 2010, pp. 1-8.
Zhu, S., et al., "Feature Selection for Gene Expression Using Model-Based Entropy", IEEE/ACM Transactions on Computational Biology and Bioinformatics, Jan.-Mar. 2010, pp. 25-36, vol. 7, No. 1.
Luo, D., et al., "SOR: Scalable Orthogonal Regression for Non-Redundant Feature Selection and its Healthcare Applications", SIAM data mining conference, Apr. 26-28, 2012, pp. 576-587.
Meyer, P., et al., "Information-Theoretic Feature Selection in Microarray Data Using Variable Complementarity," IEEE Journal of Selected Topics on Signal Processing, Jun. 2008, pp. 261-274, vol. 2, No. 3.
Liu, F., et al., "A Novel Ordering-Based Greedy Bayesian Network Learning Algorithm on Limited Data", Advances in Artificial Intelligences, Oct. 2007, pp. 80-89.
Li, J., et al., "Chap. 5: Identification of Marker Genes from High-Dimensional Microarray Data for Cancer Classification", Knowledge Discovery in Bioinformatics: Techniques, Methods, and Applications, May 2007, pp. 71-87.
El-Akadi, A., et al., "A New Gene Selection Approach Based on Minimum Redundancy-Maximum Relevance (MRMR) and Genetic Algorithm (GA)", May 10-13, 2009, pp. 69-75.
Nugraha, I., et al., "Performance Analysis of Relief and mRMR Algorithm Combination for Selecting Features in Lupus Genome-Wide Association Study," International Conference on Electrical Engineering and Informatics, Jul. 17-19, 2011, pp. 1-5.
Yu, D., et al., "Fuzzy Mutual Information Based min-Redundancy and Max-Relevance Heterogenous Feature Selection," International Journal of Computational Intelligence Systems, Jun. 2011, pp. 619-633. vol. 4, No. 4.
El-Akadi, A., "A two-stage gene selection scheme utilizing MRMR filter and GA wrapper", Knowledge and Information Systems, Mar. 2011, pp. 487-500, vol. 26, Issue 3.
Zelenak, M., et al., "Speaker overlap detection with prosodic features for speaker diarisation," IET Processing, Oct. 16, 2012, pp. 798-804, vol. 6, Issue 8.
Wikipedia., "Feature Selection," Downloaded on Mar. 26, 2015, pp. 1-16.
Wikipedia., "Hill Climbing," Downloaded Mar. 26, 2015, pp. 1-5.
Wikipedia., "Minimum redundancy feature selection," Downloaded Mar. 26, 2015, pp. 1-2.
Gayan, J., et al., "A Method for Detecting Epistasis in Genome-wide Studies Using Case-control Multi-locus Association Analysis", BMC Genomics, Jul. 2008, pp. 1-14.
Zhang, L., et al., "Modeling Haplotype-haplotype Interactions in Case-Control Genetic Association Studies", Frontiers in Genetics, Jan. 2012, pp. 1-18, vol. 3, Article 2.
Andreasen, N.C., et al., "Statistical Epistasis and Progressive Brain Change in Schizophrenia: An Approach for Examining the Relationships Between Multiple Genes", Molecular Psychiatry, Nov. 2012, pp. 1-19.
Vinh, L., et al., "A Novel Feature Selection Method Based on Normalized Mutual Information", Applied Intelligence, Aug. 23, 2011, pp. 1-21, vol. 37, Issue 1.
Zhao, Z., et al., "Advancing Feature Selection Research", ASU Feature Selection Repository, 2010, pp. 1-28.
Ma, L., et al., "Parallel and serial computing tools for testing single-locus and epistatic SNP effects of quantitative traits in genome-wide association studies", BMC Bioinformatics, Jul. 21, 2008, pp. 1-9, vol. 9, No. 1.
Dong, D., et al., Gene Expression Variations Are Predictive for Stochastic Noise, Nucleic Acids Research, 2011, B| vol. 39, No. 2, pp. 403-413; published by Oxford University Press; copyright 2010, doi:10.1093/nargkq844.
Jiang, X., et al., "Mining Pure, Strict Epistatic Interactions from High-Dimensional Datasets: Ameliorating the Curse of Dimensionality," PLOS One, www.plosone.org, Oct. 2012, vol. 7, Issue 10; e46771.
Berkeley Lectures, Jan. 8, 2011: Chapter 4 Distributed and parallel computing. Http://wla.berkeley.edu~cs61a/fa11/lectures/communication/html., last downloaded Sep. 12, 2016.

(56) References Cited

OTHER PUBLICATIONS

Gayan, J., A method for detecting epistasis in genome-wide studies using case-control multi-locus association analysis, BMC genomics, 2008年7月31日, vol. 9, p. 360.

Alquier, P., "LASSO, Iterative Feature Selection and the Correlation Selector: Oracle Inequalities and Numerical Performances." Electronic Journal of Statistics, 2:1129-1152, Aug. 2008, ISSN:1935-7524, DOI: 10.1214/08-EJS288.

Cai, Y. et al., "Prediction of Protein Subcellular Locations with Feature Selection and Analysis." Protein and Peptide Letters, 17(4):464-472, 2010, PLoS One. 2012; 7(6):e39308, published online Jun. 15, 2012. doi: 10.1371/journal.pone.0039308.

Cortes, C. et al., "On transductive regression." Advances in Neural Information Processing Systems, 19:305,2007.

Dash, M. et al.,"Feature selection for classification," Intelligent Data Analysis, 1(1-4):131-156, Mar. 1997, copyright 1997 1088-467x/97, copyright 1997.

Ding, C. et al., "Minimum redundancy feature selection from microarray gene expression data." In Bioinformatics Conference, 2003. CSB 2003. Proceedings of the 2003 IEEE, pp. 523-528. IEEE, Oct. 2003, Journal of Bioformatics and Computational Biology, vol. 3, No. 2 (2005) 185-205, Imperial College Press.

Guyon, I. et al., "An introduction to variable and feature selection. The Journal of Machine Learning Research", 3:1157-1182, Mar. 2003.

Jain, A. et al., "Feature selection: Evaluation, application, and small sample performance," Pattern Analysis and Machine Intelligence, IEEE Transactions on, 19(2):153-158, Feb. 1997.

Peng, H. et al., "Feature selection based on mutual information criteria of max-dependency, max-relevance, and min-redundancy". Pattern Analysis and Machine Intelligence, IEEE Transactions on, 27(8):1226-1238, Aug. 2005. 0162-8828/05 copyright.

Zhang, Y. et al., "Gene selection algorithm by combining relieff and mrmr." BMC genomics, 9(Suppl 2):S27, Sep. 2008. IEEE 7th International Conference in Bioformatics and Bioengineering at Harvard Medical School.

Skalak, David B., "Prototype and feature selection by sampling and random mutation hill climbing algorithms," In Proceedings of the eleventh international conference on machine learning, pp. 293-301, 1994.

Vafaie, H. et al., "Robust feature selection algorithms," In Tools with Artificial Intelligence, TAI'93, Proceedings., Fifth International Conference , pp. 356-363, IEEE, Nov. 1993.

Tsamardinos, I. et al., "The max-min hill-climbing Bayesian network structure learning algorithm," Machine learning, 65.1: 31-78. Mar. 2006. DOI 10.1007/s10994-006-6889-7.

Gammerman, A. et al., "Learning by transduction". In Proceedings of the Fourteenth Conference on Uncertainty in Artificial Intelligence, pp. 148-155. Morgan Kaufmann Publishers Inc., 1998.

Yang, Y. et al., "A comparative study on feature selection in text categorization" . In machine learning—International workshop , pp. 412-420. Morgan Kauf-mann publishers, Inc., 1997.

Farmer, M.E. et al., "Large scale feature selection using modified random mutation hill climbing," In Pattern Recognition, 2004, ICPR 2004, Proceedings of the 17th International Conference on Pattern Recognition, vol. 2, pp. 287-290, IEEE, Aug. 2004.

Haung, T. et al., "Analysis and Prediction of the Metabolic Stability of Proteins Based on Their Sequential Features, Subcellular Locations and Interaction Networks". Jun. 4, 2010. PLoS One 5(6): e10972. doi:10.1371/journal.ppone.0010972. Copyright 2010.

J.R. Kilpatrick, "Methods for detecting multi-locus genotype-phenotype association", pp. 1-152, PhD thesis, Rice University, 2009.

FEATURE SELECTION FOR EFFICIENT EPISTASIS MODELING FOR PHENOTYPE PREDICTION

CROSS-REFERENCE TO RELATED APPLICATIONS

This application is based upon and claims priority from prior U.S. patent application Ser. No. 13/745,914, filed on Jan. 21, 2013, the entire disclosure of which is herein incorporated by reference in its entirety.

BACKGROUND

The present invention generally relates to the field of computational biology, and more particularly relates to selecting features for modeling gene epistasis for phenotype prediction.

Feature selection methods are critical for classification and regression problems. For example, it is common in large-scale learning applications, especially for biological data such as gene expression data and genotype data, that where the amount of variables far exceeds the number of samples. The "curse of dimensionality" problem not only affects the computational efficiency of the learning algorithms, but also leads to poor performance of these algorithms. To address this problem, various feature selection methods can be utilized where a subset of important features is selected and the learning algorithms are trained on these features.

BRIEF SUMMARY

In one embodiment, a computer implemented method for selecting markers for modeling epistasis effects is disclosed. The computer implement method includes receiving, by a processor, a set of genetic markers and a phenotype. A relevance score is determined with respect to the phenotype for each of the set of genetic markers. A threshold is set based on the relevance score of a genetic marker in the set of genetic markers with a highest relevancy score. A relevance score is determined for at least one genetic marker in the set of genetic markers for at least one interaction between the at least one genetic marker and at least one other genetic marker in the set of genetic markers. The at least one interaction is added to a top-k feature set based on the relevance score of the at least one interaction satisfying the threshold. Each feature in the top-k feature set is one of a genetic marker and an interaction each including a top-k relevance score. A subset of the top-k feature set is selected for modeling an effect of epistasis on a physical trait.

In another embodiment, an information processing system for selecting markers for modeling epistasis effects is disclosed. The information processing system includes a memory and a processor that is communicatively coupled to the memory. A feature selection module is communicatively coupled to the memory and the processor. The feature selection module is configured to perform a method. The method includes receiving a set of genetic markers and a phenotype. A relevance score is determined with respect to the phenotype for each of the set of genetic markers. A threshold is set based on the relevance score of a genetic marker in the set of genetic markers with a highest relevancy score. A relevance score is determined for at least one genetic marker in the set of genetic markers for at least one interaction between the at least one genetic marker and at least one other genetic marker in the set of genetic markers. The at least one interaction is added to a top-k feature set based on the relevance score of the at least one interaction satisfying the threshold. Each feature in the top-k feature set is one of a genetic marker and an interaction each including a top-k relevance score. A subset of the top-k feature set is selected for modeling an effect of epistasis on a physical trait.

In a further embodiment, a non-transitory computer program product for selecting markers for modeling epistasis effects is disclosed. The computer program product includes a storage medium readable by a processing circuit and storing instructions for execution by the processing circuit for performing a method. The method includes receiving a set of genetic markers and a phenotype. A relevance score is determined with respect to the phenotype for each of the set of genetic markers. A threshold is set based on the relevance score of a genetic marker in the set of genetic markers with a highest relevancy score. A relevance score is determined for at least one genetic marker in the set of genetic markers for at least one interaction between the at least one genetic marker and at least one other genetic marker in the set of genetic markers. The at least one interaction is added to a top-k feature set based on the relevance score of the at least one interaction satisfying the threshold. Each feature in the top-k feature set is one of a genetic marker and an interaction each including a top-k relevance score. A subset of the top-k feature set is selected for modeling an effect of epistasis on a physical trait.

BRIEF DESCRIPTION OF THE SEVERAL VIEWS OF THE DRAWINGS

The accompanying figures where like reference numerals refer to identical or functionally similar elements throughout the separate views, and which together with the detailed description below are incorporated in and form part of the specification, serve to further illustrate various embodiments and to explain various principles and advantages all in accordance with the present invention, in which.

DETAILED DESCRIPTION

Figure 1:
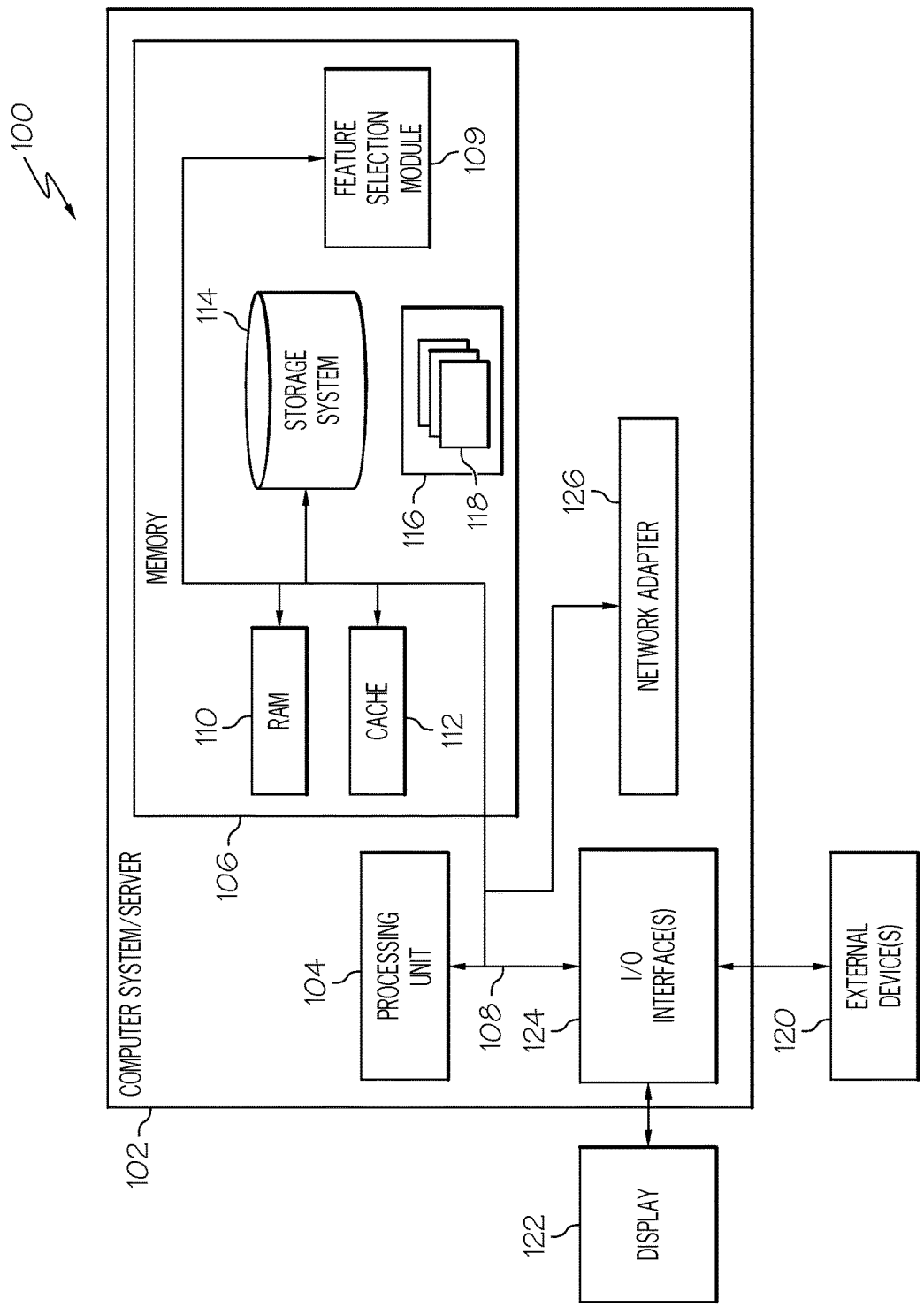
FIG. 1 is a block diagram illustrating one example of an operating environment according to one embodiment of the present invention.

FIG. 1 illustrates a general overview of one operating environment 100 according to one embodiment of the present invention. In particular, FIG. 1 illustrates an information processing system 102 that can be utilized in embodiments of the present invention. The information processing system 102 shown in FIG. 1 is only one example of a suitable system and is not intended to limit the scope of use or functionality of embodiments of the present invention described above. The information processing system 102 of FIG. 1 is capable of implementing and/or performing any of the functionality set forth above. Any suitably configured processing system can be used as the information processing system 102 in embodiments of the present invention.

As illustrated in FIG. 1, the information processing system 102 is in the form of a general-purpose computing device. The components of the information processing system 102 can include, but are not limited to, one or more processors or processing units 104, a system memory 106, and a bus 108 that couples various system components including the system memory 106 to the processor 104.

The bus 108 represents one or more of any of several types of bus structures, including a memory bus or memory controller, a peripheral bus, an accelerated graphics port, and a processor or local bus using any of a variety of bus architectures. By way of example, and not limitation, such architectures include Industry Standard Architecture (ISA) bus, Micro Channel Architecture (MCA) bus, Enhanced ISA (EISA) bus, Video Electronics Standards Association (VESA) local bus, and Peripheral Component Interconnects (PCI) bus.

The system memory 106, in one embodiment, includes a feature selection module 109 configured to perform one or more embodiments discussed below. For example, in one embodiment, the feature selection module 109 is configured to an epistasis feature selection process based on Maximum-Relevancy and Minimum Redundancy criteria. This feature selection mechanism is herein referred to as "EMRMR". As will be discussed in greater detail below, using EMRMR the feature selection module 109 selects a set of features from a feature space using Max-Relevance and Min-Redundancy criteria for efficiently modeling epistasis for phenotype prediction. It should be noted that even though FIG. 1 shows the feature selection module 109 residing in the main memory, the feature selection module 109 can reside within the processor 104, be a separate hardware component, and/or be distributed across a plurality of information processing systems and/or processors.

The system memory 106 can also include computer system readable media in the form of volatile memory, such as random access memory (RAM) 110 and/or cache memory 112. The information processing system 102 can further include other removable/non-removable, volatile/non-volatile computer system storage media. By way of example only, a storage system 114 can be provided for reading from and writing to a non-removable or removable, non-volatile media such as one or more solid state disks and/or magnetic media (typically called a "hard drive"). A magnetic disk drive for reading from and writing to a removable, non-volatile magnetic disk (e.g., a "floppy disk"), and an optical disk drive for reading from or writing to a removable, non-volatile optical disk such as a CD-ROM, DVD-ROM or other optical media can be provided. In such instances, each can be connected to the bus 108 by one or more data media interfaces. The memory 106 can include at least one program product having a set of program modules that are configured to carry out the functions of an embodiment of the present invention.

Program/utility 116, having a set of program modules 118, may be stored in memory 106 by way of example, and not limitation, as well as an operating system, one or more application programs, other program modules, and program data. Each of the operating system, one or more application programs, other program modules, and program data or some combination thereof, may include an implementation of a networking environment. Program modules 118 generally carry out the functions and/or methodologies of embodiments of the present invention.

The information processing system 102 can also communicate with one or more external devices 120 such as a keyboard, a pointing device, a display 122, etc.; one or more devices that enable a user to interact with the information processing system 102; and/or any devices (e.g., network card, modem, etc.) that enable computer system/server 102 to communicate with one or more other computing devices. Such communication can occur via I/O interfaces 124. Still yet, the information processing system 102 can communicate with one or more networks such as a local area network (LAN), a general wide area network (WAN), and/or a public network (e.g., the Internet) via network adapter 126. As depicted, the network adapter 126 communicates with the other components of information processing system 102 via the bus 108. Other hardware and/or software components can also be used in conjunction with the information processing system 102. Examples include, but are not limited to: microcode, device drivers, redundant processing units, external disk drive arrays, RAID systems, tape drives, and data archival storage systems.

One criterion for feature selection is referred to as Maximum-Relevance and Minimum-Redundancy (MRMR). MRMR greedily selects features that are maximally relevant to the class value, and are also minimally dependent on each other. In MRMR, the Maximum-Relevance criterion searches for features that maximize the mean value of all mutual information values between individual features and a class variable. However, feature selection based only on Maximum-Relevance tends to select features that have high redundancy, namely the correlation of the selected features tends to be high. If some of these highly correlated features are removed the respective class-discriminative power would not change, or would only change by an insignificant amount. Therefore, the Minimum-Redundancy criterion is utilized to select mutually exclusive features. A more detailed discussion on MRMR is given in Peng et al., "Feature selection based on mutual information criteria of max-dependency, max-relevance, and min-redundancy", Pattern Analysis and Machine Intelligence, IEEE Transactions on, 27(8): 1226-1238, 2005, which is hereby incorporated by reference in its entirety.

In a phenotype prediction problem the input is generally a set of samples each with a phenotype value, and a set of genotype values (also referred to herein as "feature", "marker", and "genotype"). The task in phenotype prediction is to use this input data to train a model so that further genotype data can be used to predict non-available phenotype data. Therefore the regression is represented as the following:

$$Y = \beta_0 + \sum_{i=1}^{d} \beta_i X_i + e \qquad (EQ\ 1)$$

where Y is the phenotype and $X_i$ is the i-th genotype value, d is the total number of genotype and $\beta_i$ is the regression coefficient for the i-th genotype, and e is the error, typically assumed to be normally distributed. As the number of genotypes usually far exceeds the number of samples, the prediction suffers the "curse of dimensionality" problem.

Epistasis is the phenomenon where different genotypes can interact with each other. With the epistasis effects, one type of epistasis regression model can be given by:

$$Y = \beta_0 + \sum_{i=1}^{d} \beta_i X_i + \sum_{i,j}^{d} \beta_{i,j} X_i X_j + e \qquad (EQ\ 2)$$

where $X_i X_j$ is the product of the genotype values of the i-th and j-th genotype and it denotes the interaction of the two genotypes. The number of all pairs of possible epistasis is $O(d^2)$, where d is the number of genotypes. Given that d is usually tens of thousands to millions, an exhaustive search is infeasible for even moderate data set. In a problem setting where the feature space is of tens of thousands to million the exhaustive search may take weeks to years to finish. Therefore, it is very important to develop more efficient methods.

Greedy strategies have been applied to epistasis effects detection where a subset of high-marginal effects markers are first selected. A statistical test for epistasis is then conducted either between all the markers in the subset or between the markers in the subset and the remaining markers. One problem with these strategies is that they generally miss all the possible epistasis between the low-marginal effects markers, which are shown to exist. Therefore, one or more embodiments provide a model where every single marker is evaluated and the probability of the marker leading to significant epistasis effects is computed. If the probability is higher than a certain threshold, then all the interactions between the marker and the remaining markers are analyzed.

In one embodiment, the feature selection module 109 receives as input a set of training samples, each including a set of features such as genetic markers and a class/target value such as a phenotype. In another embodiment, the feature selection module 109 also receives a set of test samples, each including only the same set of features as the training samples with target values missing. The number k of features to be selected is also received as input by the feature selection module 109. In one embodiment, features can be represented as rows and samples as columns. Therefore, the training and test samples comprise the same columns (features), but different rows (samples). It should be noted that in other embodiments the test samples are not received, and the EMRMR selection process is only performed on the training samples. The output of the EMRMR feature selection process performed by the feature selection module 109 is a set of features and epistasis effects (i.e., interactions). If test samples are also provided as input to the feature selection module 109, the selected set of features can be further processed to build a model to predict the missing target values of the test samples.

Based on the above input, the feature selection module 109 determines a relevance score of all the features considering only the training samples according to:

$$I(x_j^{training}; c^{training}) \quad (EQ\ 3)$$

where I is the mutual information between a given feature $x_j$ (e.g., a marker) and the class value c (e.g., a phenotype). The mutual information I of two variables x and y can be defined, based on their joint marginal probabilities p(x) and p(y) and probabilistic distribution p(x, y), as:

$$I(x, y) = \sum_{i,j} p(x_i, y_i) \log \frac{p(x_i, y_i)}{p(x_i)p(y_i)}. \quad (EQ\ 4)$$

It should be noted that other method for determining the mutual information I of variables can also be used.

The feature selection module 109 then ranks all the features using their relevance score. The feature selection module sets a threshold K according to the relevance score of the top-kth feature. This threshold prevents interactions from being selected if they have a relevance score lower than K. The threshold K is further refined to exclude interactions more effectively by adding interactions into the top-k feature set. For example, for each feature in the training samples, the feature selection module 109 analyzes the interaction between a given feature and the other features in the set of training samples. The feature selection module 109 determines a relevancy score for each of these interactions with respect to the class value, similar to that discussed above with respect to EQ 3 and EQ 4.

The feature selection module 109 then compares this relevancy score to the threshold K. If the relevancy score is greater than the threshold K the feature selection module 109 adds the interaction to the top-k feature set. The top-kth feature set is then updated by removing last feature, which is the lowest ranked feature in the top-k feature set. The threshold K is dynamically updated with the current relevance score of the kth feature in the updated feature set. Therefore, as the threshold K becomes higher, it becomes harder for an interaction to be selected, which makes the model of one or more embodiments more efficient.

It should be noted that in one embodiment, the feature selection module 109 is not required to consider all interactions between a given feature and all other features. For example, in this embodiment, the feature selection module 109 randomly samples a small number of interactions between the feature and the other features, and computes the relevance score of these sampled interactions. In particular, the feature selection module 109 assumes that all the features are independently generated. When considering a given feature the feature selection module 109 randomly samples f features from the set of all features. The relevance score of each interaction between the given feature and each of the set off selected markers is then determined similar to that discussed above.

The feature selection module 109 then assumes the relevance score of the interactions where the given feature is involved follows a normal distribution. Using the f relevance scores, the feature selection module 109 estimates the mean and the standard deviation of the normal distribution. Then using this distribution, and given the total number of features as N, the feature selection module 109 computes the probability of seeing at least one significant relevance score out of the N−1 possible interactions, where a score is significant if it is higher than the current score threshold K. If the probability is lower than a predefined threshold P, e.g., 0.005, this feature is skipped. If the probability is higher than the threshold P the feature selection module 109 considers/tests the interactions between the given feature and all the remaining features.

For example, the feature selection module 109 determines the relevance score of the interactions between the given feature and the remaining features in the set of all features similar to that already discussed above. The feature selection module 109 compares these relevance scores to the threshold K. If a relevance score is greater than the threshold K, the interaction is added to the top-kth feature set and the last feature in the set is removed. The threshold K is dynamically updated with the current relevance score of the kth feature in the updated feature set, which now includes both markers and interactions. The above process is continued until all features in the training set have been considered to produce a final set of top-k features. The feature selection module 109 then outputs the final set of top-k features.

A subset of features from the top-k features can then be selected using an MRMR process such as (but not limited to) the transductive MRMR (TMRMR) process discussed in the commonly owned and co-pending U.S. application Ser. No. 13/745,930 entitled "Transductive Feature Selection With Maximum-Relevancy and Minimum-Redundancy Criteria", which is hereby incorporated by reference in its entirety. In this embodiment, each feature in the subset of features maximizes a relevancy with the phenotype and minimizes a redundancy with respect to other selected features.

Figure 2:
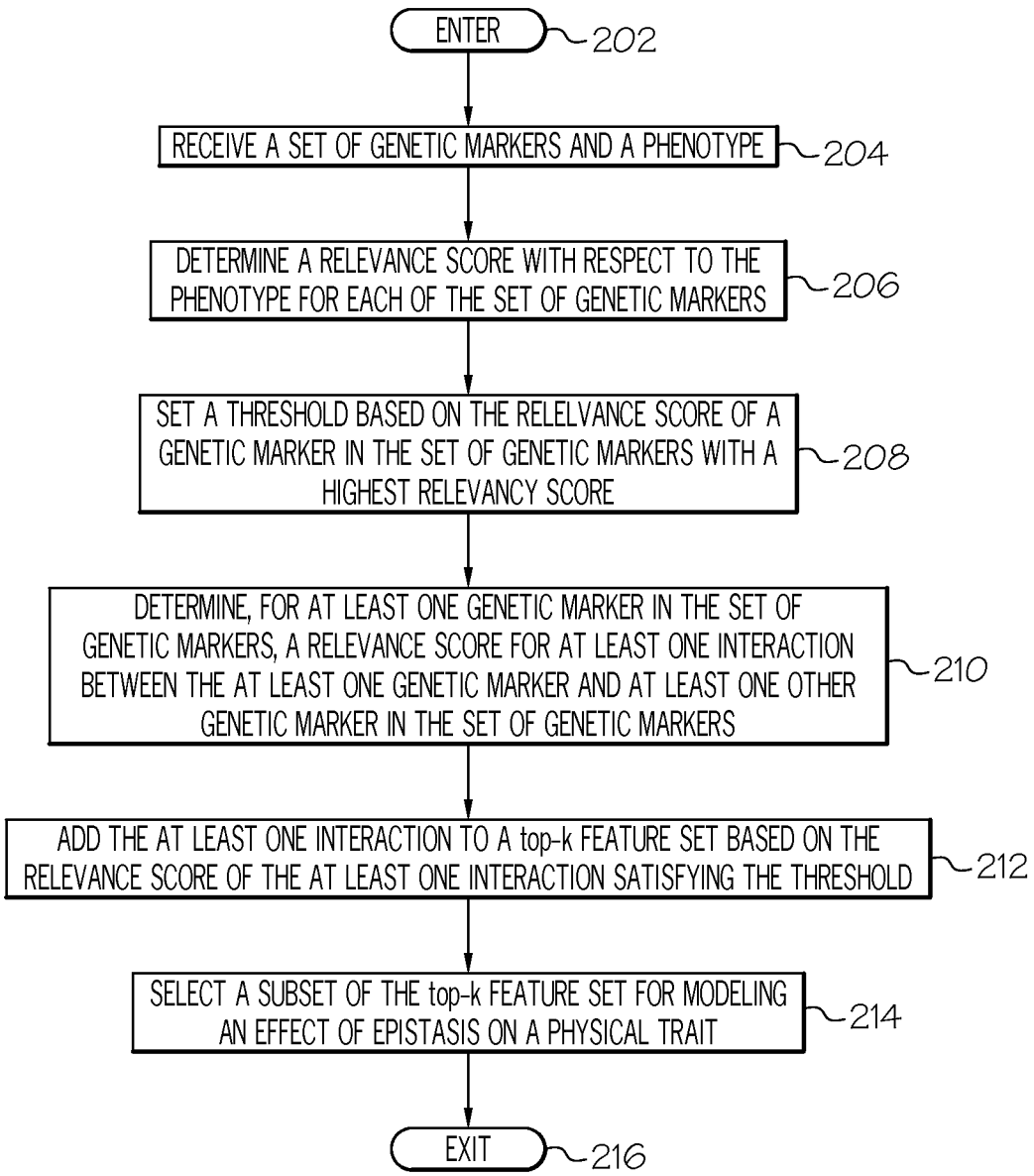
FIG. 2 is an operational flow diagram illustrating one example of selecting markers for modeling epistasis effects according to one embodiment of the present invention.

FIG. 2 is an operational flow diagram illustrating one example of an overall process for selecting markers for modeling epistasis effects. The operational flow diagram begins at step 2 and flows directly to step 204. The feature selection module 109, at step 204, a set of genetic markers and a phenotype. The feature selection module 109, at step 206, determines a relevance score with respect to the phenotype for each of the set of genetic markers. The feature selection module 109, at step 208, sets a threshold based on the relevance score of a genetic marker in the set of genetic markers with a highest relevancy score. The feature selection module 109, at step 210, determines a relevance score for at least one genetic marker in the set of genetic markers for at least one interaction between the at least one genetic marker and at least one other genetic marker in the set of genetic markers. The feature selection module 109, at step 212, adds the at least one interaction to a top-k feature set based on the relevance score of the at least one interaction satisfying the threshold. Each feature in the top-k feature set is one of a genetic maker and an interaction each including a top-k relevance score. The control flow exits at step 214.

As will be appreciated by one skilled in the art, aspects of the present invention may be embodied as a system, method, or computer program product. Accordingly, aspects of the present invention may take the form of an entirely hardware embodiment, an entirely software embodiment (including firmware, resident software, micro-code, etc.) or an embodiment combining software and hardware aspects that may all generally be referred to herein as a "circuit," "module" or "system." Furthermore, aspects of the present invention may take the form of a computer program product embodied in one or more computer readable medium(s) having computer readable program code embodied thereon.

Any combination of one or more computer readable medium(s) may be utilized. The computer readable medium may be a computer readable signal medium or a computer readable storage medium. A computer readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium may be any tangible medium that can contain, or store a program for use by or in connection with an instruction execution system, apparatus, or device.

A computer readable signal medium may include a propagated data signal with computer readable program code embodied therein, for example, in baseband or as part of a carrier wave. Such a propagated signal may take any of a variety of forms, including, but not limited to, electro-magnetic, optical, or any suitable combination thereof. A computer readable signal medium may be any computer readable medium that is not a computer readable storage medium and that can communicate, propagate, or transport a program for use by or in connection with an instruction execution system, apparatus, or device.

Program code embodied on a computer readable medium may be transmitted using any appropriate medium, including but not limited to wireless, wireline, optical fiber cable, RF, etc., or any suitable combination of the foregoing.

Computer program code for carrying out operations for aspects of the present invention may be written in any combination of one or more programming languages, including an object oriented programming language such as Java, Smalltalk, C++ or the like and conventional procedural programming languages, such as the "C" programming language or similar programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

Aspects of the present invention have been discussed above with reference to flowchart illustrations and/or block diagrams of methods, apparatus (systems), and computer program products according to various embodiments of the invention. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiment was chosen and described in order to best explain the principles of the invention and the practical application, and to enable others of ordinary skill in the art to understand the invention for various embodiments with various modifications as are suited to the particular use contemplated.

What is claimed is:

1. An information processing system for reducing search time of features in sample data and reducing computation time when training a model for generating specialized data based on the features, the information processing system comprising:
a memory;
a processor communicatively coupled to the memory; and
a feature selection circuit coupled to the memory and the processor, wherein the feature selection circuit is configured to perform a plurality of operations comprising:
receiving a set of genetic markers and a phenotype from at least one external information processing system;
training an epistasis effect model based on the set of genetic markers and the phenotype;
reducing computation time of the information processing system during the training of the epistasis effect model and further reducing feature selection time of the epistasis effect model, wherein reducing the computation time and the feature selection time comprises:
determining, for each of the set of genetic markers, a relevance score with respect to the phenotype according to $I(x_j^{training}; c^{training})$, where I is mutual information between a given genetic marker $x_j$ and a phenotype c, where mutual information I between two variables x and y is defined, based on their joint marginal probabilities p(x) and p(y) and probabilistic distribution p(x, y), as:

$$I(x, y) = \sum_{i,j} p(x_i, y_i) \log \frac{p(x_i, y_i)}{p(x_i)p(y_i)};$$

setting a threshold based on the relevance score of a genetic marker in the set of genetic markers with a highest relevancy score;
determining, for at least one individual genetic marker in the set of genetic markers having a relevance score satisfying the threshold, a relevance score for at least one interaction between the at least one individual genetic marker and at least one other individual genetic marker in the set of genetic markers;
adding the at least one interaction to a top-k feature set based on the relevance score of the at least one interaction satisfying the threshold, wherein the top-k feature set comprises one or more markers and one or more interactions, and wherein each of the one or more genetic markers and each of the one or more interactions comprises a top-k relevance score;
identifying a subset of the top-k feature set based on the set of genetic markers, wherein each feature in the subset of the top-k feature set maximizes a relevancy with the phenotype and minimizes a redundancy with respect to other selected features; and
training the epistasis effect model utilizing at least the subset of the top-k feature set, wherein the epistasis effect model predicts phenotypes for genetic markers;
storing the trained epistasis effect model in memory;
electronically obtaining, a new set of a set of genetic markers that is associated phenotype data; and
executing the trained epistasis effect model, wherein executing the trained epistasis effect model comprises
inputting the new set of genetic markers into the trained epistasis effect model; and
outputting a phenotype for the new set of genetic markers, wherein the phenotype that was outputted was not made available to the feature selection circuit as part of the new set of genetic markers.

2. The information processing system of claim 1, wherein the method further comprises:
randomly sampling a subset of genetic markers from the set of genetic markers; and
selecting the at least one additional genetic marker from the subset of genetic markers.

3. The information processing system of claim 2, wherein determining the relevance score of the at least one interaction comprises:
determining a first set of relevance scores comprising a relevance score with respect to the phenotype for each of a first plurality of interactions between the at least one genetic marker and each of the subset of genetic markers;
determining, based on a normal distribution associated with the first set of relevance scores, a probability of the at least one genetic marker being associated with an interaction comprising a relevance score greater than the threshold;
comparing the probability to a probability threshold; and
determining, based on the probability satisfying the probability threshold, a second set of relevance scores comprising a relevance score for each of a second plurality of interactions between the at least one genetic marker and a remaining set of genetic markers in the set of genetic markers, wherein the second plurality of interactions comprises the at least one interaction, and wherein the remaining set of genetic markers comprises the at least one additional genetic marker.

4. The information processing system of claim 1, wherein the method further comprises:
generating, based on adding the at least one interaction to the top-k feature set, an updated top-k feature set by removing one of a genetic marker and an interaction associated with a lowest relevance score from the top-k feature set.

5. The information processing system of claim 1, wherein the method further comprises:
updating the threshold according to a highest relevance score associated with one of a genetic marker and an interaction within the updated top-k feature;
determining a relevance score for at least one additional interaction between the at least one genetic marker and at least one other genetic marker in the set of genetic markers;
comparing the relevance score of at least one additional interaction to the threshold that has been updated; and adding the at least one additional interaction to the top-k feature set based on the relevance score of the at least one additional interaction satisfying the threshold that has been updated.

6. A non-transitory computer program product for reducing search time of features in sample data and reducing computation time when training a model for generating specialized data based on the features, the computer program product comprising:
 a storage medium readable by a processing circuit of an information processing system and storing instructions for execution by a feature selection circuit of the information processing system for performing a method comprising:
  receiving a set of genetic markers and a phenotype from at least one external information processing system;
  training an epistasis effect model based on the set of genetic markers and the phenotype;
  reducing computation time of the information processing system during the training of the epistasis effect model, and further reducing feature selection time of the epistasis effect model, wherein reducing the computation time and the feature selection time comprises:
   determining, for each of the set of genetic markers, a relevance score with respect to the phenotype according to $I(x_j^{training}; c^{training})$, where I is mutual information between a given genetic marker $x_j$ and a phenotype c, where mutual information I between two variables x and y is defined, based on their joint marginal probabilities p(x) and p(y) and probabilistic distribution p(x, y), as:

$$I(x, y) = \sum_{i,j} p(x_i, y_i) \log \frac{p(x_i, y_i)}{p(x_i)p(y_i)};$$

setting a threshold based on the relevance score of a genetic marker in the set of genetic markers with a highest relevancy score;
   determining, for at least one individual genetic marker in the set of genetic markers having a relevance score satisfying the threshold, a relevance score for at least one interaction between the at least one individual genetic marker and at least one other individual genetic marker in the set of genetic markers;
   adding the at least one interaction to a top-k feature set based on the relevance score of the at least one interaction satisfying the threshold, wherein the top-k feature set comprises one or more markers and one or more interactions, and wherein each of the one or more genetic markers and each of the one or more interactions comprises a top-k relevance score;
   identifying a subset of the top-k feature set based on the set of genetic markers, wherein each feature in the subset of the top-k feature set maximizes a relevancy with the phenotype and minimizes a redundancy with respect to other selected features; and
   training the epistasis effect model utilizing at least the subset of the top-k feature set, wherein the epistasis effect model predicts phenotypes for genetic markers;
  storing the trained epistasis effect model in memory;
  electronically obtaining, a new set of a set of genetic markers that is associated phenotype data; and
  executing the trained epistasis effect model, wherein executing the trained epistasis effect model comprises
   inputting the new set of genetic markers into the trained epistasis effect model; and
   outputting a phenotype for the new set of genetic markers, wherein the phenotype that was outputted was not made available to the feature selection circuit as part of the new set of genetic markers.

7. The non-transitory computer program product of claim 6, wherein the method further comprises:
 randomly sampling a subset of genetic markers from the set of genetic markers; and
 selecting the at least one additional genetic marker from the subset of genetic markers.

8. The non-transitory computer program product of claim 7, wherein determining the relevance score of the at least one interaction comprises:
 determining a first set of relevance scores comprising a relevance score with respect to the phenotype for each of a first plurality of interactions between the at least one genetic marker and each of the subset of genetic markers;
 determining, based on a normal distribution associated with the first set of relevance scores, a probability of the at least one genetic marker being associated with an interaction comprising a relevance score greater than the threshold;
 comparing the probability to a probability threshold; and
 determining, based on the probability satisfying the probability threshold, a second set of relevance scores comprising a relevance score for each of a second plurality of interactions between the at least one genetic marker and a remaining set of genetic markers in the set of genetic markers, wherein the second plurality of interactions comprises the at least one interaction, and wherein the remaining set of genetic markers comprises the at least one additional genetic marker.

9. The non-transitory computer program product of claim 6, wherein the method further comprises:
 generating, based on adding the at least one interaction to the top-k feature set, an updated top-k feature set by removing one of a genetic marker and an interaction associated with a lowest relevance score from the top-k feature set.

10. The non-transitory computer program product of claim 6, wherein the method further comprises:
 updating the threshold according to a highest relevance score associated with one of a genetic marker and an interaction within the updated top-k feature.

11. The non-transitory computer program product of claim 10, wherein the method further comprises:
 determining a relevance score for at least one additional interaction between the at least one genetic marker and at least one other genetic marker in the set of genetic markers;
 comparing the relevance score of at least one additional interaction to the threshold that has been updated; and
 adding the at least one additional interaction to the top-k feature set based on the relevance score of the at least one additional interaction satisfying the threshold that has been updated.

* * * * *